United States Patent [19]
Thompson et al.

[11] 4,102,195
[45] Jul. 25, 1978

[54] HOT SPOT TEMPERATURE SENSOR

[75] Inventors: John H. Thompson, Severna Park; Stephen Kowalyshyn, Columbia; Arthur Nelkin, Annapolis, all of Md.

[73] Assignee: Westinghouse Electric Corp., Pittsburgh, Pa.

[21] Appl. No.: 766,819

[22] Filed: Feb. 8, 1977

[51] Int. Cl.$^2$ ............................................. G01K 11/26
[52] U.S. Cl. ................................. 73/340; 73/339 A; 73/579
[58] Field of Search ................... 73/67.2, 339 A, 350, 73/579, 340

[56] References Cited

U.S. PATENT DOCUMENTS

| | | | |
|---|---|---|---|
| 3,318,152 | 5/1967 | Thompson et al. | 73/362.8 |
| 3,350,942 | 11/1967 | Peltola | 73/339 A |
| 3,580,058 | 5/1971 | Lynnworth | 73/67.7 |
| 3,595,069 | 7/1971 | Fowler | 73/67.2 |
| 3,633,424 | 1/1972 | Lynnworth et al. | 73/339 A |
| 3,636,754 | 1/1972 | Lynnworth et al. | 73/67.8 R |
| 3,927,570 | 12/1975 | Hedvall et al. | 73/350 |
| 3,999,433 | 12/1976 | Taplin | 73/339 A |

*Primary Examiner*—S. Clement Swisher
*Attorney, Agent, or Firm*—D. Schron

[57] ABSTRACT

A temperature sensor arrangement which utilizes high Q temperature sensitive resonators coupled to an acoustic waveguide. Several resonators, each resonant at a different frequency, are positioned at various locations in a system to be monitored and an acoustic signal is sent down the waveguide. Reflected acoustic energy is examined for the presence of the various resonant frequencies. Since the resonant frequency of each resonator is temperature sensitive, the detected signals provide an indication of temperature at the respective various locations.

23 Claims, 15 Drawing Figures

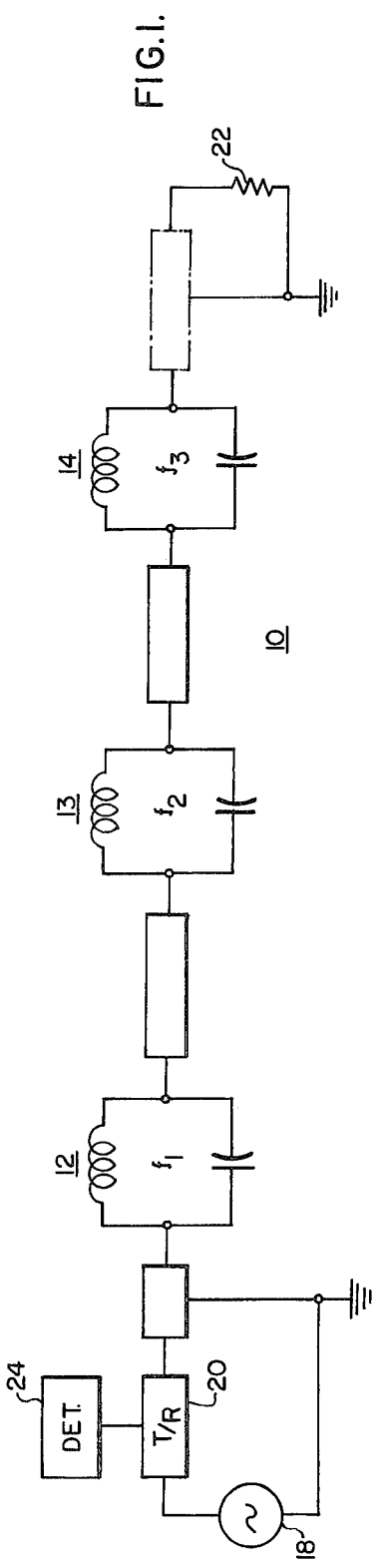
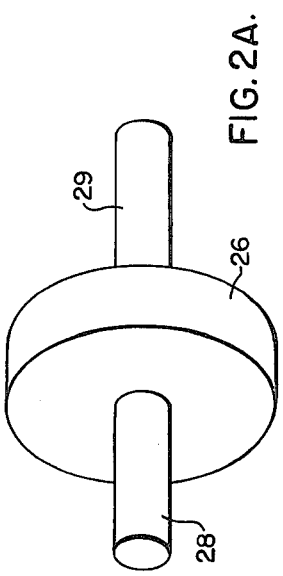
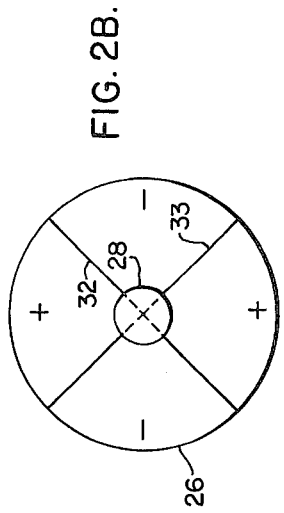
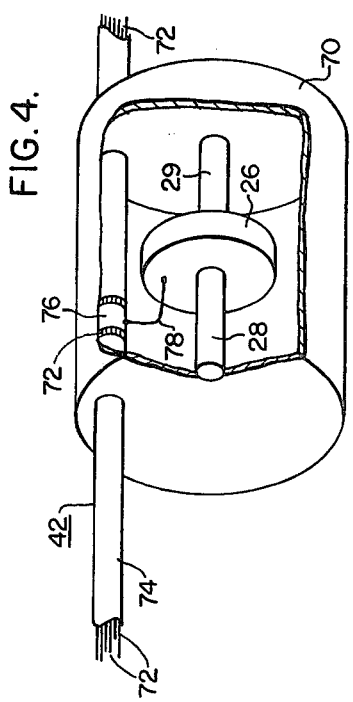
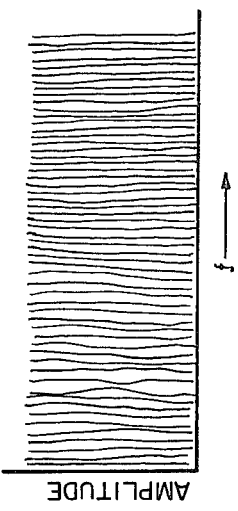

HOT SPOT TEMPERATURE SENSOR

BACKGROUND OF THE INVENTION

1. Field of the Invention

The invention in general relates to temperature sensing apparatus, and particularly to such apparatus utilizing acoustics.

2. Description of the Prior Art

In the operation of industrial apparatus, it is often desired to know the temperature at various locations within the apparatus itself. One simple method of accomplishing this temperature sensing is by the use of thermistors which may be placed at various desired locations. The themistors provide respective output signals indicative of the localized temperature and these signals are conducted by means of wires to a central location for utilization of the information.

For some types of apparatus, for example, high voltage power transformers, the utilization of thermistors with wires leading to the transformer tank wall would be highly undesirable.

To eliminate the requirement for low voltage signal carrying wires extending to the transformer tank wall, proposals have been made for temperature sensors which incorporate a radio transmission unit. The sensor includes a frequency determining element which varies in accordance with the temperature and receiver apparatus at the tank wall, receives the transmitted signal, which is an indication of the temperature in the vicinity of the sensor. Various points in the transformer may be monitored by utilization of various sensors operating at respectively different frequencies.

The costs of these radio transmission sensors can be extremely high due to the required ultrahigh reliability and for many transformers the maintenance required for proper operation of these radio transmitting sensors is not justified.

The present invention provides a sensing system particularly useful for high voltage transformers and in which the sensing apparatus within the transformer tank is passive, and without the requirement of any metallic connection to the transformer tank wall.

SUMMARY OF THE INVENTION

A temperature sensing system is provided which includes an acoustic waveguide and a transmitting means coupled to the waveguide for transmitting an acoustic signal down the waveguide. At least one mechanical resonator is placed at a location, the temperature of which is to be detected, with the resonator being of the type having a resonant frequency which changes with temperature. Means are provided for coupling the acoustic signal in the waveguide to the resonator which will then reflect back up the waveguide any acoustic signal of a frequency equal to the then resonant frequency of the resonator. The reflected back signal is then detected and processed to provide an indication of temperature.

In a transformer environment, a plurality of resonators is provided, each enclosed in its own respective housing and each preferably being of the flexural disc type. A single acoustic waveguide may be provided to pass through the housings of the resonators and acoustic signal transfer between the waveguide and the disc resonator takes place within the housing.

A directional coupler arrangement is provided whereby only a reflected signal is conducted to detection apparatus, to the exclusion of a transmitted signal. The arrangement includes means for obtaining an indication of force due to the acoustic energy and of velocity of the acoustic energy.

BRIEF DESCRIPTION OF THE DRAWINGS

FIG. 1 is a circuit representing the electrical analogy of the electromechanical system of the present invention;

FIG. 2A is a perspective view of a flexural mode resonator and FIG. 2B is a plan view thereof;

FIG. 4 is a view, with a portion broken away, of the resonator of FIG. 2A contained within a housing;

FIG. 5 illustrates the frequency spectrum of the signal source of FIG. 3;

DESCRIPTION OF THE PREFERRED EMBODIMENT

Figure 3:
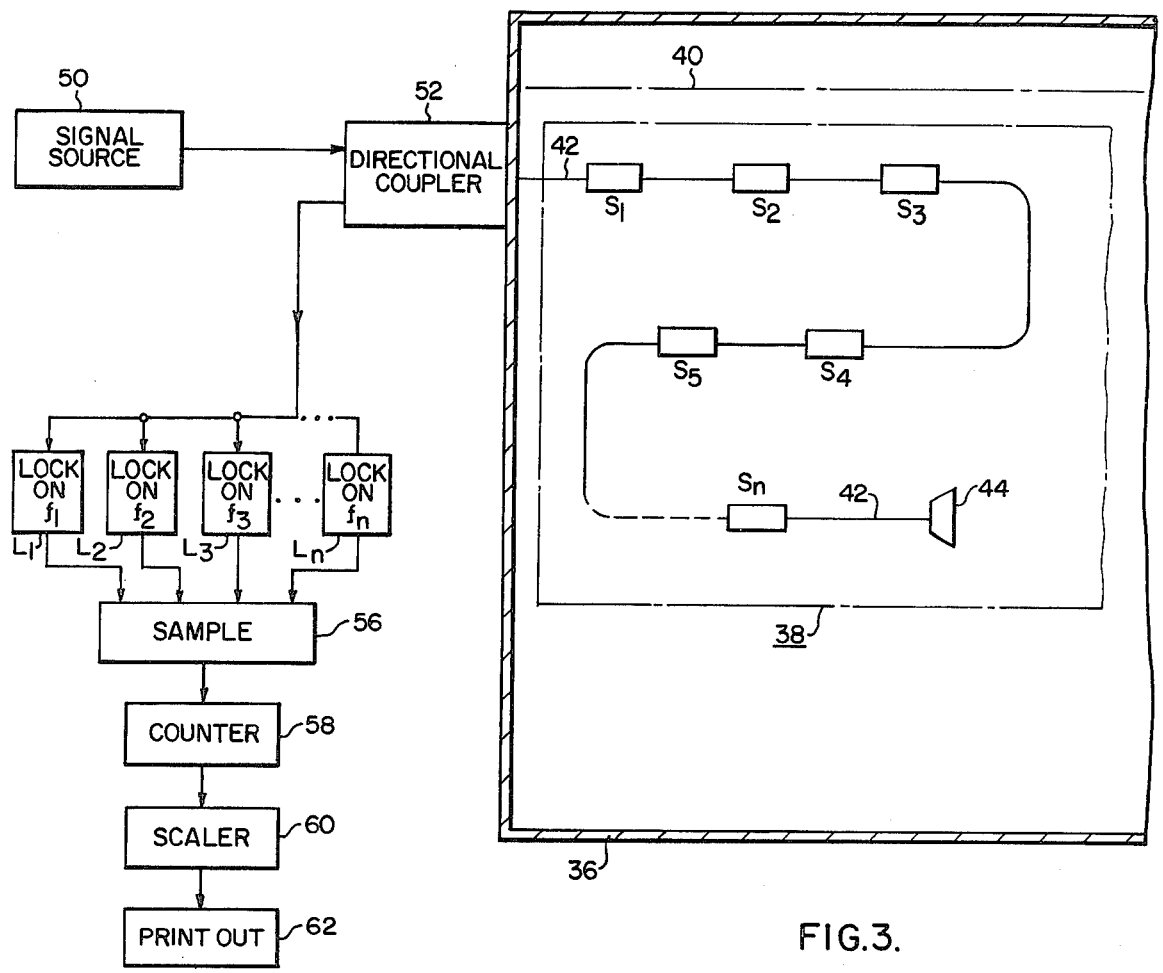
FIG. 3 is a block diagram illustrating the temperature sensing system in conjunction with a high voltage transformer.

FIG. 1 serves to basically illustrate the principle of operation of the present electromechanical system, utilizing an electrical analogy. In FIG. 1 a transmission line 10 includes a plurality of serially arranged LC resonant circuits 12, 13 and 14, each resonant at a respective frequency $f_1$, $f_2$ and $f_3$.

A signal generator 18 provides a signal including frequencies $f_1$, $f_2$ and $f_3$ to transmission line 10 through a T/R (transmit/receive) switch 20, and the opposite end of the transmission line is terminated by characteristic impedance 22 which effectively prevents any reflection of all the frequencies transmitted.

Resonant circuit 12 presents an extremely high impedance to a signal of frequency $f_1$ such that all other frequencies continue their transmission down the transmission line while the signal frequency $f_1$ is reflected back up the transmission line and may be detected by detector 24. In a similar manner, resonant circuit 13 will reflect back a signal frequency $f_2$ while passing all other signals and resonant circuit 14 will reflect back a signal frequency $f_3$.

The present invention does not use LC resonant circuits but rather mechanical resonators, a preferred example of which is illustrated in FIGS. 2A and 2B. The mechanical resonator is of the flexural mode type which by way of example includes a flexural mode disc 26 made of a high heat conductive metal, such as aluminum or titanium. Integral with the disc 26 is a support means which takes the form of high heat conductive posts 28 and 29 having a lossless bond with the disc 26.

In its oscillatory flexural mode of operation, disc 26 includes first and second nodal diameters 32 and 33 which divide the disc into four equal quadrants such that the two positive quadrants simultaneously project axially in one direction while the two negative quadrants project in an opposite direction. On a different half cycle the quadrants reverse their directions. Such discs are well known and are further described in U.S. Pat. No. 3,318,152 which is herein incorporated by reference.

The construction of the resonator is such as to provide an extremely high Q, for example in the tens of thousands range, and the resonant frequency is a function of temperature. The resonant frequency of the resonator may be defined by:

$$f_r = .238 \frac{t}{r^2} \sqrt{\frac{Y}{\rho(1 - \sigma^2)}}$$

where:
$f_r$ = resonant frequency (Hz)
$t$ = disc thickness (cm)
$r$ = disc radius (cm)
$\rho$ = mass density (grams per cc)
$Y$ = Young's modulus (dynes per square cm)
$\sigma$ = Poisson's ratio.

Although the present invention finds use with a variety of systems in which temperature is to be measured, it is particularly well adapted for use in conjunction with high voltage transformer apparatus for measuring the temperature at various locations within the transformer tank. With reference to FIG. 3, a portion of a transformer wall 36 is illustrated with the interior thereof containing transformer equipment generally indicated by the dotted line 38 (windings, etc.) and which equipment is immersed in a transformer oil 40.

Positioned throughout the equipment at various locations in the windings is a plurality of sensor units $S_1$, $S_2$, $S_3$ ... $S_n$, each including a mechanical resonator such as in FIG. 2A and each being coupled to an acoustic waveguide 42 which is terminated at its far end by an acoustic termination 44.

A signal source 50 provides, in one embodiment, an output noise signal (white noise) containing frequencies including those at which the sensors are resonant. This signal is converted into a corresponding acoustic signal by directional coupler 52 and applied to the acoustic waveguide 42.

Directional coupler 52 also functions in the nature of a T/R switch by directing reflected back signals to detection circuitry including a plurality of lock-on circuits $L_1$ through $L_n$, one for each expected return frequency. Each lock-on circuit is constructed and arranged to detect a particular resonant frequency (plus or minus some frequency change due to temperature variations). The output signal from each individual lock-on circuit, therefore, is a frequency associated with a particular sensor and indicative of the temperature which that particular sensor is experiencing.

A sample switch 56 is operable to scan the outputs of the lock-on circuits and provide in sequence each individual output to a counter circuit 58, the output signal of which is provided to scaler circuit 60 where the equivalent temperature for the particular count is derived. In most instances, a visual indication of a particular sensor's temperature will be provided by a print-out circuit 62 although any other signals provided can be utilized in conjunction with a computer for determination of such items as loading based upon temperature, making possible more economical and safer use of the transformer, estimation of remaining thermal life of the insulation of the transformer windings, following a known history of loading, or even assist in the possible redesign of coil cooling features to provide for more uniform temperature distribution, to name a few.

FIG. 4 illustrates a typical sensor S, of the sensor array of FIG. 3, utilizing a flexural disc resonator as in FIG. 2A. The resonator 26 is protected from the ambient oil by means of a housing 70 (broken away in FIG. 4) and the end portions of which support the posts 28 and 29.

Acoustic waveguide 42 is made up of a plurality of nonmetallic fibers 72, one example being glass fibers commonly used in fiber optic applications. The glass fibers 72 are tightly encased in a jacket 74 of some compliant material such as plastic tubing.

Within the housing 70 means are provided for coupling the acoustic signal and the acoustic waveguide to the resonator 26. Inside housing 70 the glass fibers 72 are connected, such as by means of epoxy, to a plate 76 of a material having a similar acoustic impedance as the glass fiber bundle so as to minimize acoustic mismatch and consequent reflection. One example of such material is glass. The acoustic waveguide continues with the glass fibers being glued to the other side of plate 76. The acoustic transmission line is coupled to disc 26 by means of a compliant member 78 which effectively decouples the line from the frequencies off resonance. Near resonance a frequency exists for which the disc has a motional mass reactance which resonates with the compliant member 78, making the impedance very high to the transmission line at a particular resonance, and thus causing reflections at this frequency. Compliant member 78 may simply be a wire made out of aluminum, and bonded to plate 76 and resonator 26.

Figure 6:
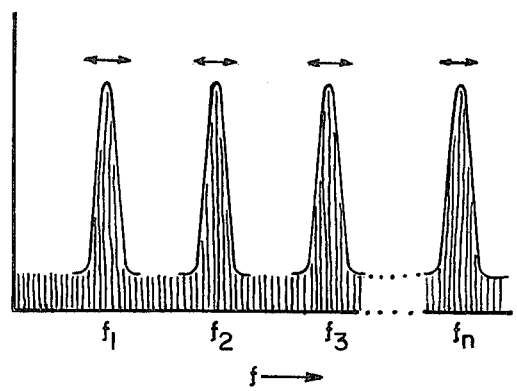
FIG. 6 illustrates frequency signals returned back up the acoustic waveguide of FIG. 3.

FIG. 5 illustrates the frequency spectrum of the transmitted acoustic signal utilizing a white noise source. In response to such signal, the sensors will reflect back a frequency spectrum as illustrated in FIG. 6 where it is seen that the amplitude peaks at certain frequencies $f_1$, $f_2$, $f_3$ ... $f_n$ representing the respective resonant frequencies of the $n$ sensors. During normal operation, these peaks may move slightly over a range, as indicated by the arrows, indicating a change in temperature and the flexural discs resonators are constructed so that there is adequate separation between resonant frequency ranges. The position of each peak is a function of the temperature of its respective sensor and the width of each peak is a function of the Q of its respective resonator, the higher the Q, the narrower the peak, hence the desirability of very high Q resonators.

Figure 7:
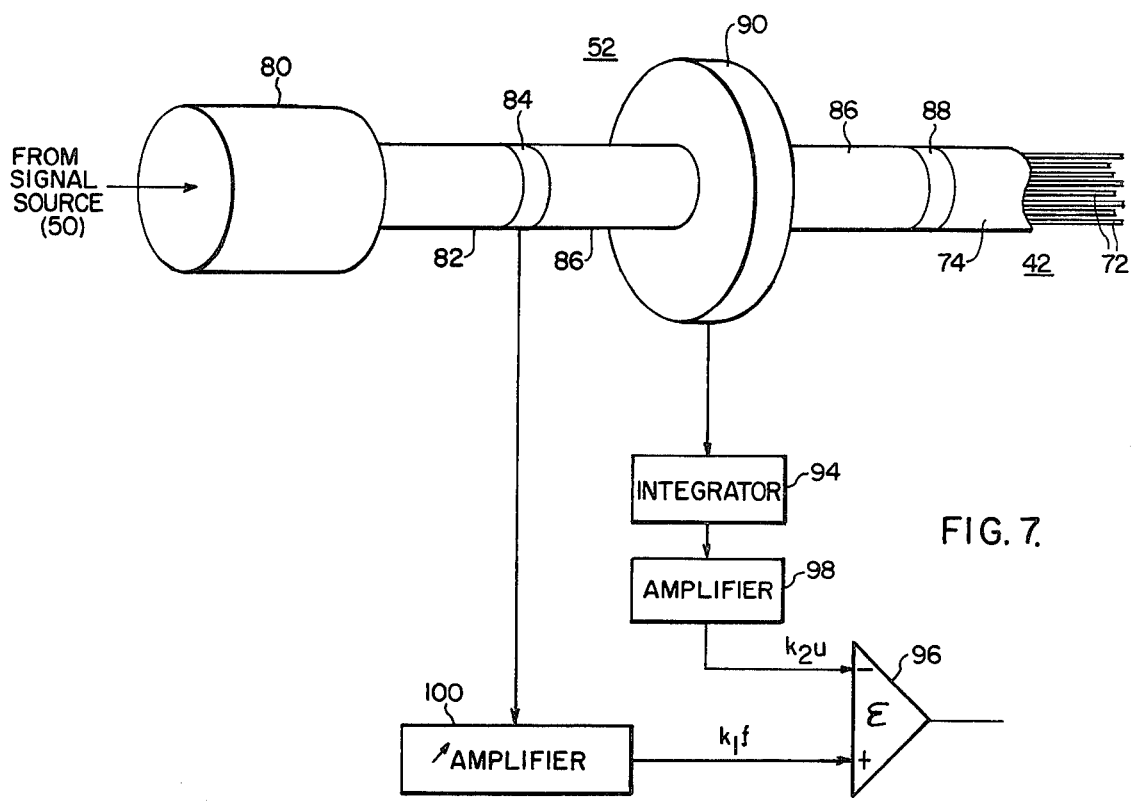
FIG. 7 illustrates a portion of the apparatus of FIG. 3 in more detail.

FIG. 7 illustrates one embodiment of a directional coupler which may be utilized herein. The coupler 52 includes a transmitting transducer 80 which receives the white noise from signal source 50 to provide an acoustic version thereof. One type of transducer which will serve this purpose is the Tonpilz transducer having a head mass, tail mass, and an intermediate motor generator section. The radiating member (the head mass in the case of a Tonpilz) is coupled to a rigid pipe 82, such as aluminum, and which is connected to a force sensor 84, such as a piezoceramic transducer.

Rigid pipe 86 connected to the other side of force sensor 84 terminates in a coupler plate 88 and to which is connected the acoustic waveguide 42, such as by having the glass fibers 72 glued thereto. Surrounding pipe section 86 and connected thereto is a piezoelectric accelerometer 90 operating in a shear mode to derive a signal proportional to the acceleration of the acoustic waves in pipe section 86.

The principle of operation with the arrangement of FIG. 7 may be easily understood by considering its electrical analog in which force is voltage and velocity is current. For a signal going from left to right:

$$u = f/R_o$$

where $u$ = velocity; $f$ = force; $R_o$ = mechanical characteristic impedance.

Force sensor 84 in conjuction with amplifier 100 provides a voltage proportional to the force, and is designated $k_1f$ in FIG. 7. Accelerometer 90 provides an acceleration signal which in conjunction with integrator 94 and amplifier 98 provides a voltage $k_2u$, proportional to the acoustic signal velocity. The waveguide arrangement has an acoustic termination equivalent to being terminated in its characteristic impedance so that the gain of the amplifiers may be adjusted such that $$k_1f = k_2u.$$

Accordingly, the output of summation circuit 96 is $k_1f-k_2u = 0$. There is, therefore, no output signal in response to an acoustic signal traveling from transmitting transducer 80 to the acoustic waveguide and sensors.

Figure 8A:
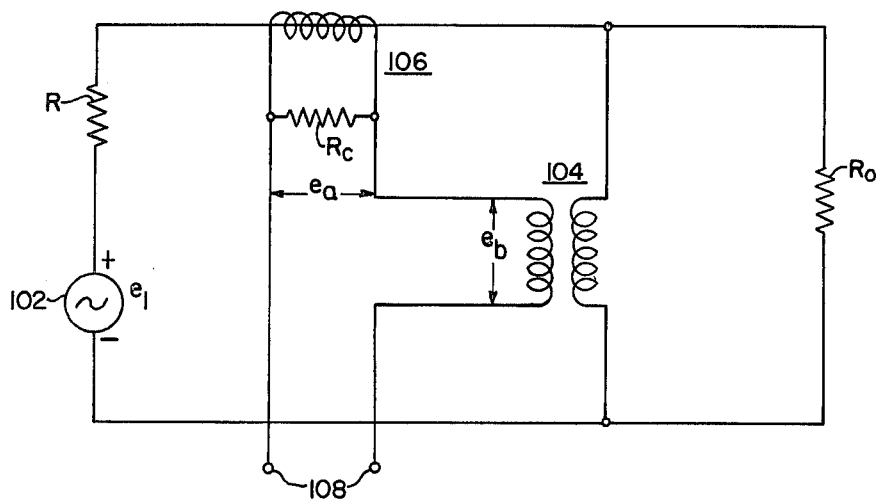
FIGS. 8A and 8B are electrical circuit diagrams illustrating the principle of operation of the directional coupler network of FIG. 3.

The electric analogy is illustrated in FIG. 8A wherein generator 102 represents the transmitted acoustic signal source, with R being some internal resistance. The circuit includes resistance $R_o$, the characteristic impedance, and further includes a voltage transformer 104 and a current transformer 106 having a resistance $R_c$ across the windings thereof. Current transformer 106 and the secondary of voltage transformer 104 are connected in series and to output terminals 108. If $e_1$ is the voltage of generator 102, then the current flow $i$ is equal to:

$$i = e_1/R+R_o.$$

Suppose, by way of example that $e_1$ is 100 volts and $R_o$ and R have the same value of 50 ohms. The current accordingly would be 1 amp. If the current transformer 106 is adjusted so that it puts out a voltage $e_a$ of 1 volt for 1 amp of current and the voltage transformer 104 provides an output $e_b$ of 1 volt on the secondary side for 50 volts on the primary side, then the voltage from the current sensor would be 1 volt and the voltage from the voltage sensor would be 1 volt, resulting in an output of $1 - 1 = 0$ at terminals 108.

Figure 8B:
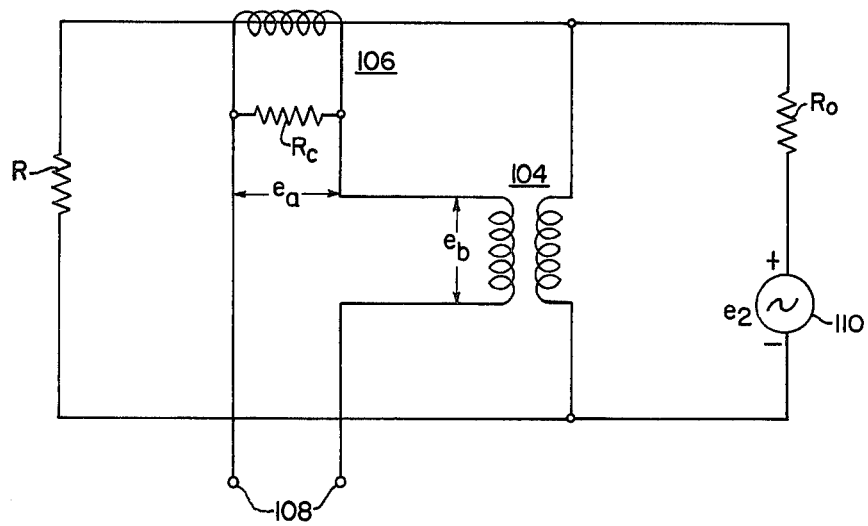

In FIG. 8B the reflected signal from the sensors is treated as a separate source and is indicated by the voltage generator 110. Suppose, by way of example, that the voltage $e_2$ of generator 110 is 25 volts. In such instance, the current would be $25 \div 100 = .25$ amps and the voltage across the primary of voltage transformer 104 would be equivalent to $e_2$ minus the voltage drop across $R_o$ or 12.5 volts. Since the voltage transformer 104 provides a 50 to 1 transformation, the voltage at the secondary of transformer 104 would be 1/50th of 12.5 volts, or 0.25 volts. Since the current in the circuit is 0.25 amps, the voltage produced by current transformer 106 would be 0.25 volts and the total voltage appearing at output terminal 108 is now additive because of the direction change of the current and would be equal to 0.25 + 0.25, or 0.5 volts.

It is to be noted that for convenience the values of $R_o$ and R were chosen to be equal. The previous treatment and results are the same, even for different values. For example, suppose that $R_o$ was 50 ohms and R was 25 ohms. The current in FIG. 8A for these values, therefore, would be $100 \div 75 = 1.33$ amps and the voltage across the primary of voltage transformer 104 would be $1.33 \times 50$ or 66.667 volts. The voltage of the secondary would be 1/50th of that or 1.333 volts. Since the current sensor has a 1 to 1 ratio, the voltage produced by it would also be 1.33 volts and the difference would still be 0.

Referring once again to FIG. 7, since accelerometer 90 provides a signal proportional to acceleration, an integrator circuit 94 is provided to derive from the acceleration signal, a signal which is proportional to velocity. This velocity signal is provided to summation circuit 96 after amplification in amplifier 98 while the force signal from force sensor 84 is provided to summation circuit 96 after amplification in amplifier 100. The signal from amplifier 98 is analogous to voltage $e_a$ of FIGS. 8A and 8B while the output of amplifier 100 is analogous to voltage $e_b$. By properly adjusting the relative gain of the amplifiers, the output of summation circuit 96 may be made substantially zero when accelerometer 90 is accelerated in a first direction by the transmitted signal, with the net result being a multifrequency output signal when the accelerometer is accelerated in an opposite direction by the acoustic energy reflected back up the acoustic waveguide from the various resonators.

Figure 9:
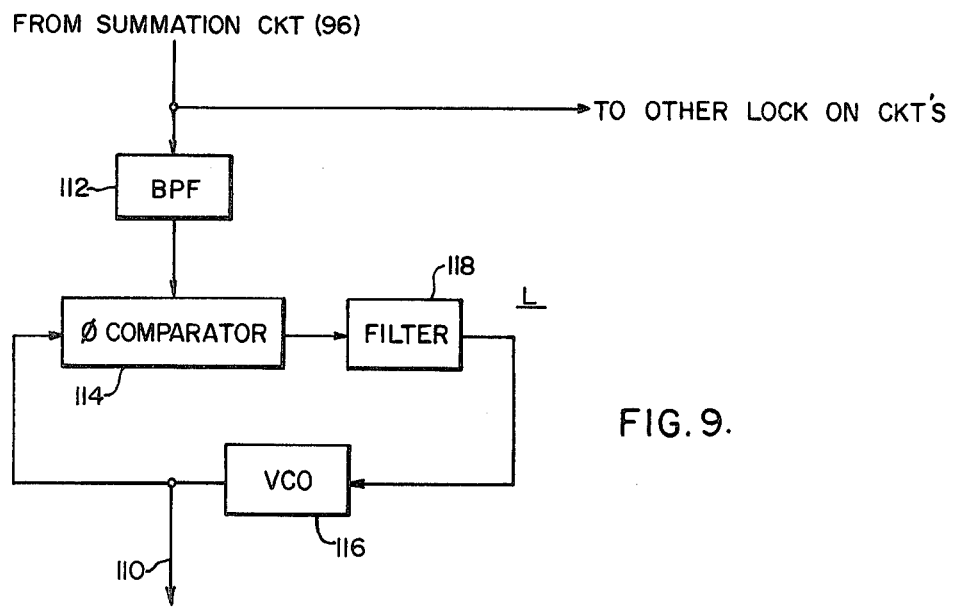
FIG. 9 is a block diagram illustrating the lock-on circuits of FIG. 3 in more detail.

FIG. 9 illustrates in somewhat more detail a typical lock-on circuit L of FIG. 3. The reflected signal from the various resonators as provided from the summation circuit 96 (FIG. 7) is provided to a bandpass filter 112 for initially filtering the signal so that only a certain predetermined band of frequencies corresponding to a predetermined range of resonant frequency of a particular sensor, is passed. This signal is provided to phase comparator circuit 114, an additional input of which is provided by a voltage controlled oscillator (VCO) 116 operable to provide an output signal. If the VCO output frequency is the same as the frequency of the input signal, then the phase comparator 114 will not provide an output correction signal. If the VCO output frequency is not the same as the frequency at the input signal, then the phase comparator 114 will provide an output signal, which is filtered in filter circuit 118, to provide a DC control signal for VCO to adjust its frequency until it agrees with that of the input signal. Such operation is extremely well known to those skilled in the art and may be identified by the term "phase locked loop". The VCO output therefore on line 110 is equal to the frequency of the input signal and the frequency thereof is indicative of the temperature of a particular sensor, and it is this signal on line 110 which is sampled and processed by the apparatus illustrated in FIG. 3. It is to be noted that the circuitry illustrated in FIG. 9 is merely representative of a single lock-on circuit and that additional similar circuits would normally be provided in a multisensor array with the circuits having different band-pass characteristics as well as different VCO frequency ranges.

Figure 10:
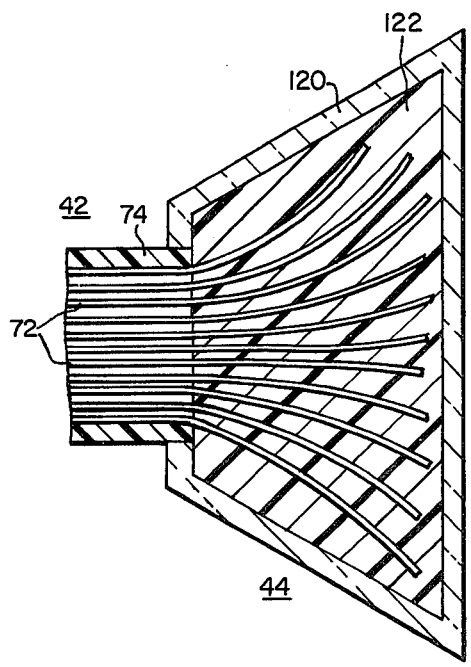
FIG. 10 is a cross-sectional view of the acoustic waveguide and its termination.

Since operation is predicated upon energy reflected back up the acoustic waveguide, it is important that an acoustic mismatch not occur at the far end of the waveguide which would cause the various frequency signals to be reflected back to the detecting apparatus, thus possibly causing erroneous readings. In order to prevent this, the waveguide is provided with the acoustic termination 44 as illustrated in FIG. 10. The acoustic termination 44 includes a housing member 120 made of a nonmetallic material, such as plastic or ceramic. Tubing 74 of the acoustic waveguide 42 extends through an aperture in housing 120 and is secured thereto with the glass fibers 72 being spread out into the housing which contains an acoustic absorbing material 122, one example being butyl rubber.

Figure 11:
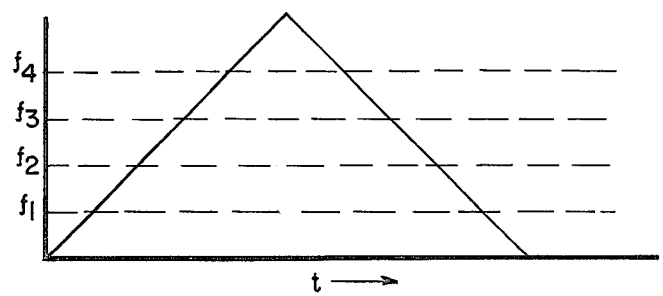
FIG. 11 illustrates an alternate signal source.
Figure 12:
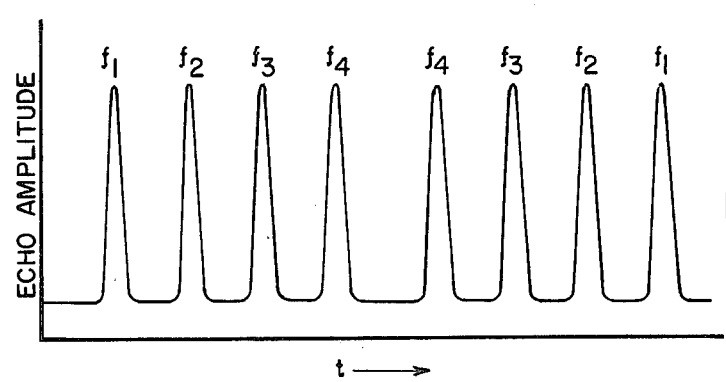
FIG. 12 illustrates the signals reflected back up the waveguide, utilizing the signal source of FIG. 11.

FIG. 5 illustrated the noise signal produced by the signal source 50 of FIG. 3 and encompassing the frequency range of operation of all the resonators utilized. As an alternative, the signal source 50 may provide a signal such as in FIG. 11 wherein the frequency is plotted on the vertical axis and time on the horizontal axis. Basically, the signal source is designed to provide a signal, the frequency of which varies as a function of time, with the frequency range being chosen in accordance with the operating frequencies of the individual resonators utilized. Thus, for the signal of FIG. 11, echo amplitudes as a function of time will be received, as illustrated in FIG. 12. For a system utilizing four resonators, the reflected resonant frequencies will be provided sequentially as illustrated, and lock-on circuitry similar to that already described may be provided for the proper interpretation of the reflected signals.

Figure 13:
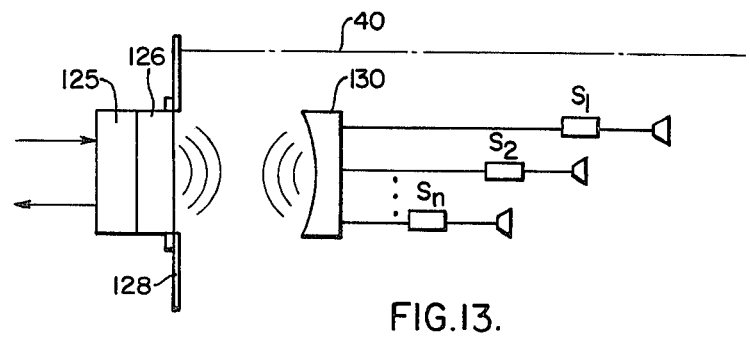
FIG. 13 illustrates an alternate arrangement of coupling acoustic energy.

In the embodiment of FIG. 3 the acoustic signal from and to the directional coupler was carried by means of an acoustic waveguide extending from the sensor array to the transformer wall. FIG. 13 illustrates an alternate embodiment which eliminates this connection. In the embodiment of FIG. 13, a directional coupler 125 is connected to an acoustic projector/receiver 126 connected to the transformer wall 128. Acoustic energy is then propagated through the transformer oil to a second projector/receiver 130 which then provides the projected acoustic energy to the sensor array.

Although the sensor array could be serially arranged, as in FIG. 3, FIG. 13 shows an alternate embodiment wherein the sensors $S_1$ to $S_n$ are arranged in parallel to simultaneously receive the projected acoustic signal, with each sensor being connected to the projector/receiver 130 by means of a previously described acoustic waveguide with each having a respective acoustic termination as in FIG. 10.

The reflected acoustic signals from the respective resonators are transmitted back up the respective acoustic waveguides to the projector/receiver 130 which then transmits the signal through the transformer oil to the projector/receiver 126 where the signal is detected and processed.

We claim:
1. A temperature sensing system, comprising:
(A) an acoustic waveguide;
(B) transmitting means coupled to said acoustic waveguide for transmitting a continuous wave acoustic signal down said acoustic waveguide;
(C) a mechanical resonator having a resonant frequency which varies with temperature;
(D) a compliant coupling member for coupling said acoustic signal in said acoustic waveguide to said resonator which will then reflect back up said acoustic waveguide any acoustic signal of a frequency equal to the then resonant frequency of said resonator; and
(E) means for detecting and processing the reflected back signal.
2. Apparatus according to claim 1 which includes:
(A) a plurality of said resonators, each resonant at a different frequency; and
(B) means for coupling each of said plurality of resonators to said acoustic waveguide.
3. Apparatus according to claim 1 which includes:
(A) a plurality of said resonators, each resonant at a different frequency;
(B) a plurality of said acoustic waveguides;
(C) means for coupling each of said plurality of resonators to a respective one of said plurality of acoustic waveguides.
4. Apparatus according to claim 1 wherein:
(A) said resonator is a high Q frequency disc resonator having two nodal diameters.
5. Apparatus according to claim 4 which includes:
(A) at least one heat conducting post integral with said disc at the intersection of said nodal diameters.
6. Apparatus according to claim 5 which includes:
(A) a housing member;
(B) said resonator being contained in and supported by said housing member.
7. Apparatus according to claim 6 wherein:
(A) said acoustic waveguide passes through said housing member.
8. Apparatus according to claim 6 wherein:
(A) said housing member is constructed and arranged to exclude the ambient medium in which it is immersed.
9. Apparatus according to claim 4 wherein:
(A) said acoustic waveguide is comprised of a plurality of nonmetallic sections.
10. Apparatus according to claim 9 wherein:
(A) said nonmetallic sections are each comprised of a bundle of glass fibers.
11. Apparatus according to claim 10 which includes:
(A) a compliant tubing covering said bundle of glass fibers.
12. A temperature sensing system, comprising:
(A) an acoustic waveguide comprised of a plurality of nonmetallic sections each section comprised of a bundle of glass fibers;
(B) transmitting means coupled to said acoustic waveguide for transmitting an acoustic signal down said acoustic waveguide;
(C) a high Q flexural mode disc resonator having two nodal diameters and having a resonant frequency which varies with temperature;
(D) means for coupling said acoustic signal in said acoustic waveguide to said resonator which will then reflect back up said acoustic waveguide any acoustic signal of a frequency equal to the then resonant frequency of said resonator, and including
(i) a plate;
(ii) a first nonmetallic section of said acoustic waveguide being coupled to one side of said plate;
(iii) a second nonmetallic section being coupled to the other side of said plate; and
(iv) a wire connected to and between said plate and one surface of said high Q flexural disc; and
(E) means for detecting and processing the reflected back signal.
13. Apparatus according to claim 1 which includes:

(A) an acoustic termination at the end of said acoustic waveguide remote from said transmitting means and operable to absorb acoustic energy to prevent acoustic reflection.

14. Apparatus according to claim 1 wherein said transmitting means includes:
(A) an electric signal source;
(B) a transducer connected to receive the electric output signal of said source to provide an acoustic signal; and
(C) means for conveying said acoustic signal to said acoustic waveguide.

15. Apparatus according to claim 14 wherein:
(A) said electric signal source provides a white noise signal.

16. Apparatus according to claim 14 wherein:
(A) said electric signal source provides a signal, the frequency of which varies with time and the frequency range of which encompasses the range of expected resonant frequencies of said resonator.

17. A temperature sensing system, comprising:
(A) an acoustic waveguide;
(B) transmitting means coupled to said acoustic waveguide for transmitting an acoustic signal down said acoustic waveguide and including
 (i) an electric signal source;
 (ii) a transducer connected to receive the electric output signal of said source to provide an acoustic signal; and
 (iii) means for conveying said acoustic signal to said acoustic waveguide;
(C) a mechanical resonator having a resonant frequency which varies with temperature;
(D) means for coupling said acoustic signal in said acoustic waveguide to said resonator which will then reflect back up said acoustic waveguide any acoustic signal of a frequency equal to the then resonant frequency of said resonator; and
(E) means for detecting and processing the reflected back signal and including
 (i) a directional coupler coupled to said transmitting means and said acoustic waveguide and operable to provide substantially a signal indicative of only a reflected back signal and not of a transmitted signal.

18. Apparatus according to claim 17 wherein said directional coupler includes:
(A) a force transducer connected to said means for conveying for providing an output signal indicative of the force of acoustic signals within said means for conveying;
(B) an accelerometer connected to said means for conveying for providing an output signal indicative of the acceleration of acoustic signals within said means for conveying;
(C) an integrator connected to receive said accelerometer output signal to provide a velocity signal;
(D) amplifier means for adjusting the relative gain of said force and velocity signals; and
(E) means for combining said force and velocity signals for providing a summed output signal.

19. Apparatus according to claim 18 which includes:
(A) a frequency lock-on circuit for each said resonator used;
(B) each said lock-on circuit being responsive to said summed output signal for providing a respective frequency signal indicative of the then resonant frequency of a respective resonator.

20. Apparatus according to claim 19 which includes:
(A) means for converting each said frequency signal into a corresponding temperature indication.

21. Apparatus for measuring the temperature within the windings of an oil filled transformer having a tank wall comprising:
(A) a plurality of mechanical resonators positioned at various points within said windings with each said resonator having a resonant frequency which varies with temperature;
(B) transmitting means located exteriorly of said wall for generating a continuous wave acoustic signal;
(C) detecting and processing means located exteriorly of said wall;
(D) acoustic waveguide means having nonmetallic sections exposed to said oil coupled to receive said acoustic signal;
(E) compliant coupling members for coupling said acoustic signal in said acoustic waveguide means to respective ones of said resonators;
(F) said resonators thereupon being operable to reflect respectively unique signals back up said acoustic waveguide means; and
(G) means for coupling said reflected signals to said detecting and processing means.

22. Apparatus according to claim 21 wherein:
(A) said acoustic waveguide means is a single waveguide which extends from said resonators within said windings to said wall.

23. Apparatus according to claim 21 which includes:
(A) a first acoustic projector/receiver mounted on said wall;
(B) a second acoustic projector/receiver located interiorly of said tank;
(C) said transmitting means being coupled to said first projector/receiver;
(D) said acoustic waveguide means being coupled to said second projector/receiver;
(E) said first and second projector/receivers being positioned to transmit acoustic signals to each other.

* * * * *